United States Patent [19]

Mielke et al.

[11] Patent Number: 4,664,913
[45] Date of Patent: May 12, 1987

[54] METHOD FOR TREATING PLASMA FOR TRANSFUSION

[75] Inventors: C. Harold Mielke, San Rafael; Patrick J. Scannon, Davis; Paul R. Sohmer, Los Angeles; John C. Klock, Mill Valley, all of Calif.

[73] Assignee: Xoma Corporation, Berkeley, Calif.

[21] Appl. No.: 632,756

[22] Filed: Jul. 19, 1984

Related U.S. Application Data

[63] Continuation-in-part of Ser. No. 381,499, May 24, 1982, abandoned.

[51] Int. Cl.⁴ ............................................. A61K 35/16
[52] U.S. Cl. ..................................... 424/101; 424/85; 424/88; 604/5; 604/6
[58] Field of Search ................. 424/101; 435/268, 269; 604/5, 6

[56] References Cited

PUBLICATIONS

Bensinger et al.—Transfusion (Phila.), vol. 21, No. 3 (1981), pp. 335–342.
Bensinger et al.—Progress in Clinical & Biol. Res., vol. 88 (1982), pp. 295–300.
Bensinger—Artificial Organs, vol. 5(3), 1981, pp. 254–258.
Bystryn et al.—J. of Exptl. Med., vol. 132, No. 6, Dec. 1970, pp. 1279–1287.
Graf et al.—J. Exp. Med., vol. 130 (1969), pp. 1175–1179 & 1185.

*Primary Examiner*—Sam Rosen
*Attorney, Agent, or Firm*—Townsend & Townsend

[57] ABSTRACT

A method for treating human blood plasma which comprises passing plasma through an immunoadsorbent zone capable of binding both anti-A and anti-B blood group antibodies and removing them from the plasma. Plasma so treated may be transfused to any recipient regardless of the recipient's blood type, and it is found that such treated plasma retains substantially all other blood proteins essential for proper physiological activity.

8 Claims, No Drawings

METHOD FOR TREATING PLASMA FOR TRANSFUSION

The present application is a continuation-in-part of application Ser. No. 381,499, filed on May 24, 1982, now abandoned.

BACKGROUND OF THE INVENTION

1. Field of the Invention

The present invention is a method for treating human blood plasma prior to administering to a patient and, more particularly, is a method for removing blood group antibodies from the plasma to avoid incompatibility between donors and recipients of different blood groups.

Blood is a heterogeneous system in which a variety of cells are suspended in an aqueous solution (plasma) composed of proteins, lipoproteins and lipids in colloidal suspension and organic metabolites in solution. The cells include red cells (erythrocytes), white cells (leukocytes) and platelets (thrombocytes). Plasma is the solution which remains after the cells have been removed from the blood. Present in the plasma are various proteins, including antibodies secreted by the white cells as an immunological response to the presence of antigens in the blood, as well as proteins responsible for other essential physiological processes, such as the clotting factors required for hemostasis.

The major human blood group or type is determined by the presence of ABH antigens on the cell surface of the red blood cells. The antigens are oligosaccharides attached to glycolipids or glycoproteins in the plasma membranes of the red blood cells. The antigenic structure is of three types, referred to as "A", "B" and neither "A" nor "B" (that is "H" or formerly "O"). Either the A antigen, the B antigen, or both the A and B antigen may be present on the surface of an individual's red blood cells. Every individual's blood will contain naturally occurring antibody (primarily IgM) against the ABH antigens which are not present on his red blood cells. The situation is summarized in Table 1, which follows.

TABLE 1

| Blood Group | Antigen On Red Cell | Antibodies In Blood |
|---|---|---|
| A | A substance | anti-B |
| B | B substance | anti-A |
| AB | Both A and B substance | Neither anti-A nor anti-B |
| H or O | Neither A nor B substance (H substance) | Both anti-A and anti-B |

Individuals suffering from trauma which results in the loss of blood often require the transfusion of blood or blood plasma to compensate for the blood loss. Blood plasma is often used in place of whole blood because it is easier to store.

When transfusing plasma, incompatibility between the donor and the recipient arises whenever the donor's blood (and therefore plasma) includes antibodies to the ABH antigens, if any, present on the recipient's red blood cells. For example, plasma from a donor having group A blood cannot be transfused into a recipient having group B blood since the donor's plasma includes anti-B antibodies which would react with the recipient's blood. Thus, plasma from a donor having group H blood, which includes both anti-A and anti-B antibodies is incompatible with a recipient having any blood type other than H. Conversely, plasma from a donor having AB blood, which includes neither anti-A nor anti-B antibodies, is compatible with any recipient, regardless of blood group. Because of the potential for incompatibility, it has heretofore been necessary to carefully segregate the various types of plasma and maintain them separately so that plasma is not transfused into an incompatible recipient.

For the above reasons, it would be desirable to provide a treatment for removing the antibodies to the incompatibility antigens from plasma to provide a "universal" plasma which could be administered to any recipient regardless of blood type. Such treatment, however, must be highly specific to ensure that essential blood proteins, particularly the clotting factors, are not removed or inactivated. At present, there are at least 13 known clotting factors. Interference with the activity of any one of these factors in the transfused plasma could reduce the ability of the recipient's blood to clot. This is a serious problem since most plasma recipients are suffering from trauma which requires that their clotting function be unimpaired.

2. Description of the Prior Art

The use of immunoadsorption for the specific removal of anti-A or anti-B antibodies from the blood of patients about to undergo bone marrow transplants is known. See, Bensinger, et al., (1981) "Immunoadsorption for Removal of A and B Blood-Group Antibodies," N. Engl. J. Med., 304: 160-162; Bensinger (1981) Artificial Organs 5: 254-258; Bensinger et al. (1981) Transfusion 21: 355-342; and, Bensinger et al. (1982) Progress in Clinical and Biological Research 88: 295-300.

SUMMARY OF THE INVENTION

The present invention provides a method for treating human plasma obtained from any donor which renders the plasma or product compatible with any recipient, regardless of the recipient's blood group. The method comprises passing plasma from the donor through an immunoadsorbent zone capable of binding one or more of the antibodies to remove such antibodies. The immunoadsorbent zone includes receptors specific for both the anti-A and anti-B antibodies, typically anti-(anti-A) and anti-(anti-B) antibodies or the A and B antigens themselves, immobilized therein. The method requires that the ABH antibodies be substantially completely removed from the product to at least below a level detectable by the standard antiglobulin (Coombs) test at a 1:2 dilution, preferably at a 0 dilution.

Surprisingly, it has been found that this treatment does not substantially reduce the concentration of other blood proteins, particularly clotting factors, necessary for biological functioning of the plasma in the recipient.

DESCRIPTION OF THE PREFERRED EMBODIMENT

The present invention provides a source of human plasma derived from donors having all blood groups, which may be transfused to recipients regardless of blood group. The method may be practiced in a hospital or blood bank to avoid having to segregate plasma by blood group for storage so that a particular plasma is not administered to a recipient having an incompatible blood type. The method will also find use under emergency situations where a limited number of blood donors are available and where, in the absence of such a treatment method, plasma might be unavailable for certain individuals needing transfusions.

The method of the present invention employs an immunoadsorbent zone having receptor specific for at least anti-A or anti-B antibodies, preferably having receptors for both such antibodies, immobilized therein. By passing human plasma through the immunoadsorbent zone, the antibodies responsible for blood group incompatibilities are substantially completely removed and the plasma may be administered to any recipient, regardless of the recipient's blood type.

A. Preparation of the Immunoadsorbent Zone

1. Prepare Receptors for Anti-A and Anti-B Antibodies

The receptors may be naturally occurring or synthetic compounds which have the capability of specifically binding the anti-A and anti-B antibodies and which may be immobilized within a permeable medium to form the immunoadsorbent zone. Particularly useful are naturally occurring A and B cell surface antigens, and antibodies raised against both the anti-A and anti-B antibodies, that is, anti-(anti-A) and anti-(anti-B) antibodies. Such antibodies may be obtained in a conventional manner by hyperimmunizing any one of various mammals, such as rabbits, sheep, mice, goats, and the like, and purifying the antisera obtained. Alternatively, monoclonal antibodies may be produced by the method described by Kohler and Milstein, (1976) Nature 356: 495–497. Such techniques for preparing antibodies are well known in the art and do not form part of the present invention.

The preferred receptors for the present invention are artificially synthesized human blood group A and B antigens prepared in the manner described by Lemieux, "Human Blood Groups and Carbohydrate Chemistry," (1978) Chem. Soc. Rev., pp 423–452.

2. Solid Phase Immunoadsorbent Material

The immunoadsorbent zone of the present invention comprises the receptor immobilized on a solid phase immunoadsorbent material. Such solid phase material may be selected from a wide variety of materials, typically silicates or water insoluble polymers used to load a separation column, or water permeable membranes. In general, the immobile solid phase of the present invention must be capable of covalently or non-covalently binding the specific receptors for the anti-A and anti-B antigens and must be biocompatible with human blood.

Suitable materials include silica gels, glass beads, cross-linked dextrans, polyacrylamides and other biologically inert materials which can be derivatized, typically aminated, for immobilizing the receptors of interest.

3. Immobilization of Receptors in Immunoadsorbent Zone

The receptors may be immobilized in the immunoadsorbent zone by a variety of conventional techniques, depending in particulare on the nature of the binding material. In general, it is necessary to modify one or more functionalities on the immunoadsorbent material to allow coupling to the receptor. The covalent binding of proteins to immunoadsorbent materials, in particular antibodies, is taught in U.S. Pat. Nos. 3,555,143 and 4,108,974.

For example, artificial antigen (Lemieux, supra) includes a glycosidic union to the 8-methoxycarbonyloctyl alcohol which can serve as a bridging arm for attachment to the solid support. The antigen is reacted with acyl hydrazide to form the acyl azide which is then allowed to react with an aminated solid support or with a suitable amine or any solid material.

B. Treatment of Plasma

1. Separation of Plasma from Whole Blood

The plasma is obtained by separating the red cells, white cells and platelets from the whole blood by well-known techniques. Once the plasma is obtained, it may be treated directly or may be stored and treated at a later time.

2. Apply Plasma to the Immunoadsorbent Zone

Prior to passing plasma therethrough, the immunoadsorbent column or membrane is preferably treated to inhibit non-specific protein adsorption. This may be accomplished by washing the immunoadsorbent zone with a colloidal xylan solution (collodion) or with a saline solution containing 1% human serum albumin, and incubating the zone, preferably overnight, with the wash solution at 4° C. The column is then washed with saline solution prior to treatment of the plasma.

The plasma is passed through the immunoadsorbent zone at a rate chosen so that the final concentration of anti-A and anti-B antibodies is undetectable by the standard antiglobulin (Coombs) test at a maximum dilution of 1:2, preferably at a zero dilution. The standard antiglobulin (Coombs) test is described in Mollison, (1972) "Blood Transfusion in Clinical Medicine," Blackwell Scientific Publications, Oxford pp. 420–428.

After such treatment, the plasma or plasma fraction can be stored or used in the conventional manner. In the case of the blood products, particularly antihemophilic factor, activated prothrombin complex and the like, it will often be desirable to further treat the product, such as by lyophilization, to inhibit degradation.

The following examples are offered by way of illustration, not by way of example.

EXPERIMENTAL

Materials and Methods

Carbohydrate antigen (B-trisaccharide) prepared as described by Lemieux, supra, was bound to crystalline silica (synsorb A) and unhaptenated silica (Chembiomed, Ltd., Edmonton, Canada) according to the manufacturer's recommendations. One gram of the silica with 10 micromoles of bound antigen were placed in a cartridge suitable for passing plasma.

Plasma was obtained from ten normal, healthy donors, free from all medication for at least 14 days. Plasma (10 ml) from each donor was applied to a fresh cartridge over a five minute period, and the treated samples collected for analysis.

Results

Both treated and untreated plasma samples from each donor were tested for anti-B antibody titer by the standard antiglobulin (Coombs) test, described above. The results are set forth in Table 1. The removal of the antibody is highly efficient, with the post-treatment titer being 1:2 or below.

TABLE 1

| Donor | Anti-B Titer | |
|---|---|---|
| | Pre-treatment | Post-treatment |
| 1 | 1:64 | 1:2 |
| 2 | 1:32 | 0 |
| 3 | 1:32 | 0 |
| 4 | 1:16 | 0 |

TABLE 1-continued

| Donor | Anti-B Titer | |
|---|---|---|
| | Pre-treatment | Post-treatment |
| 5 | 1:16 | 0 |
| 6 | 1:16 | 0 |
| 7 | 1:16 | 1:2 |
| 8 | 1:8 | 0 |
| 9 | 1:8 | 0 |
| 10 | 1:8 | 0 |

Coagulation parameters were also measured, as set forth in Table 2. The values given are the average for all ten donors. Prothrombin time is the time required to convert prothrombin to thrombin. No significant deterioration was observed in this parameter. PTT is partial thrombo-plastin time. Although there was some increase in this parameter which may be attributable to partial adsorption of one or more clotting factors, the increase is not clinically significant. Similarly, the decreases in Factor VIII (antihemophilic factor), Factor V (proaccelerin), and fibrinogen, are likely due to non-specific adsorption, but are well within the limits for useful plasma.

TABLE 2

| Coagulation Parameters | Pre-treatment | Post-treatment |
|---|---|---|
| Prothrombin Time (second) | 12.5 ± 1.0 | 12.6 ± 1.1 |
| PTT (second) | 27.1 ± 2.0 | 40 ± 7 |
| Fibrinogen (mg/dl) | 230 ± 20 | 170 ± 30 |
| Factor V (%) | 95 ± 3 | 82 ± 4 |
| Factor VIII | 125 ± 5 | 75 ± 10 |

Table 3 sets forth the concentrations of immunoglobulins and ratio of albumins to globulins in the plasma before and after treatment. The drop in IgM levels (and to a lesser extent IgG levels) is to be expected since the anti-(ABH antigen) antibodies are primarily IgM. The reduction in immunoglobulins would also account for the increase in the albumin/globulin ratio.

TABLE 3

| Parameter | Pre-treatment | Post-treatment |
|---|---|---|
| IgG (mg/dl) | 800 ± 75 | 801 ± 19 |
| IgA (mg/dl) | 122 ± 12 | 158 ± 14 |
| IgM (mg/dl) | 205 ± 8 | 94 ± 11 |
| Albumin/globulin | 1.43 ± .08 | 1.75 ± .12 |

Table 4 sets forth the results of quantitative electrophoretic measurement of five specific proteins, as well as total protein, in both pre-treatment and post-treatment plasma. The average value for all ten donors is given. The only significant change is found in the decrease of immunoglobulins, as would be expected since the process is directed at immunoglobulin removal.

TABLE 4

| Protein | Pre-treatment | Post-treatment |
|---|---|---|
| Total protein (g/dl) | 6.9 ± 1.3 | 6.6 ± 0.2 |
| Albumin (g/dl) | 4.01 ± 0.31 | 4.11 ± 0.29 |
| Alpha-1-globulin (g/dl) | 0.17 ± 0.19 | 0.17 ± 0.37 |
| Alpha-2-globulin (g/dl) | 0.61 ± 0.31 | 0.59 ± 0.21 |
| Beta globulin (g/dl) | 0.62 ± 0.3 | 0.66 ± 0.64 |
| Gamma globulin (g/dl) | 1.19 ± 0.12 | 1.05 ± 0.70 |

Table 5 shows the effect of both pre-treatment and post-treatment plasma on platelet aggregation and serotonin release, in the presence of known activating factors (adenosine diphosphate (ADP), epinephrine, T50 max, and collagen). The effect of the treatment on these essential clotting functions is not significant.

TABLE 5

| | Pre-treatment | Post-treatment |
|---|---|---|
| Platelet Aggregation (%) | | |
| 5 mm ADP | 85 ± 5 | 85 ± 3 |
| 1:100 Epinephrine | 92 ± 2 | 95 ± 3 |
| T50 max | 81 ± 4 | 81 ± 3 |
| Collagen | 78 ± 4 | 81 ± 2 |
| Serotonin Release (%) | | |
| 5 mm ADP | 18 ± 2 | 19 ± 2 |
| 1:100 Epinephrine | 25 ± 3 | 24 ± 2 |
| T50 | 19 ± 2 | 21 ± 3 |
| Collagen | 42 ± 4 | 44 ± 3 |

Accordingly, a method is provided for treating blood plasma to substantially completely remove anti-(ABH antigen) antibodies from plasma prior to transfusion. Such treated plasma can be administered to recipients without regard to blood type. Surprisingly, the treated plasma retains substantially all other blood proteins measured from the standpoint of clinical significance, ensuring that the plasma will be fully capable of physiological activity in the recipient.

Although the foregoing invention has been described in some detail by way of illustration and example for purposes of clarity of understanding, it will be obvious that certain changes and modifications may be practiced within the scope of the appended claims.

What is claimed is:

1. A method for treating human blood plasma from a donor prior to transfusion to a recipient to prevent ABH blood group incompatibility, regardless of the recipient's blood type, said method employing an immunoadsorbent zone including receptors consisting essentially of receptors specific for both anti-A and anti-B antibodies immobilized therein, said method comprising:

passing the plasma through the immunoadsorbent zone so that substantially all of said anti-A and anti-B antibodies are specifically removed from the plasma without reducing the concentrations of blood factors below levels necessary for blood clotting in the transfusion recipient.

2. A method for treating human blood from a donor to produce plasma suitable for transfusion to a recipient having any ABH blood type, said method employing an immunoadsorbent zone including receptor consisting essentially of receptor capable of binding both anti-A and anti-B antibodies, said method comprising:

separating substantially all blood cells and platelets from the blood to form plasma;

passing the plasma through the immunoadsorbent zone so that substantially all anti-A and anti-B antibodies are removed without reducing the concentrations of blood factors below levels necessary for blood clotting in the transfusion recipient; and collecting the plasma to provide a source of plasma suitable for transfusion to recipients regardless of the recipient's blood group.

3. A method for transfusing plasma from a donor to a recipient, regardless of ABH blood group incompatibility, said method employing an immunoadsorbent zone containing receptor consisting essentially of receptor capable of binding both anti-A and anti-B antibodies, said method comprising:

passing the plasma through the immunoadsorbent zone under conditions such that substantially all anti-A and anti-B antibodies are removed from the plasma without reducing the concentrations of blood factors below levels necessary for blood clotting in the transfusion recipient; and transfusing the plasma to a patient.

4. A method as in claims 1, 2 or 3, wherein both the anti-A and anti-B antibodies are removed to a concentration undetectable by a standard antiglobulin (Coombs) test at a dilution of 1:2.

5. A method as in claims 1, 2 or 3, wherein the receptor in the immunoadsorbent zone includes A and B antigens.

6. A method as in claims 1, 2 or 3, wherein the receptor in the immunoadsorbent zone includes anti-(anti-A) and anti-(anti-B) antibodies.

7. A method as in claims 1, 2 or 3, wherein the immunoadsorbent zone comprises receptor immobilized on an insoluble, biocompatible solid support.

8. A method as in claims 1, 2 or 3, wherein the immunoadsorbent zone comprises receptors immobilized in a permeable membrane.

* * * * *

REEXAMINATION CERTIFICATE (1201st)

United States Patent [19]

Mielke et al.

[11] B1 4,664,913

[45] Certificate Issued Jan. 30, 1990

[54] METHOD FOR TREATING PLASMA FOR TRANSFUSION

[75] Inventors: C. Harold Mielke, San Rafael; Patrick J. Scannon, Davis; Paul R. Sohmer, Los Angeles; John C. Klock, Mill Valley, all of Calif.

[73] Assignee: Xoma Corporation, San Francisco, Calif.

Reexamination Request:
No. 90/001,722, Feb. 27, 1989

Reexamination Certificate for:
Patent No.: 4,664,913
Issued: May 12, 1987
Appl. No.: 632,756
Filed: Jul. 19, 1984

Related U.S. Application Data

[63] Continuation-in-part of Ser. No. 381,499, May 24, 1982, abandoned.

[51] Int. Cl.[4] .............................................. A61K 35/16
[52] U.S. Cl. ..................................... 424/101; 424/85; 424/88; 604/5; 604/6
[58] Field of Search ..................... 424/101; 604/5, 6

[56] References Cited

U.S. PATENT DOCUMENTS

| | | | |
|---|---|---|---|
| 4,137,401 | 1/1979 | Lemieux et al. | 536/116 |
| 4,195,174 | 3/1980 | Lemieux et al. | 536/18 |

FOREIGN PATENT DOCUMENTS

0108658  5/1984  European Pat. Off. .

OTHER PUBLICATIONS

Bernoco et al., "Specific removal of anti-red cell blood group activity from anti-HLA lymphocytotoxic sera and purification of anti-A and anti-B antibodies with lymphocytotoxic activity," *Tissue Antigens* 26:147–152 (1985).

Osterwalder et al., "Immunoadsorption for Removal of Anti-A and Anti-B Blood Group Antibodies in ABO-Incompatible Bone Marrow Transplantation," *Blut* 53:379–390 (1986).

Bensinger, E. J. et al, *New Eng J Med* (1981) 304:160–162, "Immunoadsorption for Removal of A and B Blood Group Antibodies".

Printed brochure Chembiomed Ltd. revised Sep. 1982.

Chang, TMS, *Trans Am Soc Artif. Int. Org.* (1980) XXVI:57–60, "Blood Compatible Coating of Synthetic Immunoadsorbents".

Crawford, G. et al, *Blood Transfusion & Immun.* XXIV:281–286 (1981), "Practical Application of Synthetic A and B Blood Group Immunoadsorbents".

*Primary Examiner*—Sam Rosen

[57] ABSTRACT

A method for treating human blood plasma which comprises passing plasma through an immunoadsorbent zone capable of binding both anti-A and anti-B blood group antibodies and removing them from the plasma. Plasma so treated may be transfused to any recipient regardless of the recipient's blood type, and it is found that such treated plasma retains substantially all other blood proteins essential for proper physiological activity.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *